United States Patent [19]

Gottlieb et al.

[11] Patent Number: 5,013,546

[45] Date of Patent: * May 7, 1991

[54] METHODS FOR MODULATING ANTIBODY PRODUCTION IN TREATING PATIENTS WITH AIDS, ARC AND OTHER DISEASES

[75] Inventors: A. Arthur Gottlieb, New Orleans; Robert C. Sizemore, Metarie, both of La.

[73] Assignee: Imreg, Inc., New Orleans, La.

[*] Notice: The portion of the term of this patent subsequent to Dec. 1, 2004 has been disclaimed.

[21] Appl. No.: 501,973

[22] Filed: Mar. 29, 1990

Related U.S. Application Data

[63] Continuation of Ser. No. 235,475, Aug. 23, 1988, abandoned, which is a continuation-in-part of Ser. No. 13,067, Feb. 10, 1987, abandoned.

[51] Int. Cl.$^5$ .................... A61K 37/02; A61K 45/05
[52] U.S. Cl. ................... 424/85.1; 424/85.8; 424/88; 514/18; 514/19
[58] Field of Search .......... 424/85.1, 85.8, 88; 514/18, 19

[56] References Cited

U.S. PATENT DOCUMENTS

| | | | |
|---|---|---|---|
| 4,428,938 | 1/1984 | Kisfaludy et al. | 530/330 |
| 4,468,379 | 8/1984 | Gottlieb | 424/88 |
| 4,616,079 | 10/1986 | Gottlieb | 530/344 |
| 4,699,898 | 10/1987 | Gottlieb | 514/18 |
| 4,710,380 | 12/1987 | Gottlieb | 424/101 |
| 4,751,216 | 6/1988 | Gottlieb | 514/18 |

OTHER PUBLICATIONS

Rudinger, Peptide Hormone, Parsons (ed.), Univ. Park Press, Baltimore, pp. 1-7 (1976).
Talmadge et al., Immunopharmacology, 13th International Congress of Chemotherapy, Herberman (ed.), Vienna, pp. 203/18-203/35 (1983).
Rao et al., The New England Journal of Medicine, vol. 310, p. 669 (3/15/84).

*Primary Examiner*—John Doll
*Assistant Examiner*—Christina Chan
*Attorney, Agent, or Firm*—Richard H. Stern

[57] ABSTRACT

Methods and compositions are described for increasing and decreasing immunoglobulin production by administering to a human or other mammalian subject an appropriate dosage of amplifier. Administration of amplifier to subjects having excessive production of immunoglobulin, namely AIDS and ARC patients, is shown as decreasing such excessive immunoglobulin production in such patients.

4 Claims, No Drawings

METHODS FOR MODULATING ANTIBODY PRODUCTION IN TREATING PATIENTS WITH AIDS, ARC AND OTHER DISEASES

This is a file wrapper continuation of application Ser. No. 07/235,475 (abandoned), filed Aug. 23, 1988 which was a continuation-in-part of application Ser. No. 07/013,067 (abandoned), filed Feb. 10, 1987, and applicants claim the benefit of such filing date.

BACKGROUND

Amplifiers of the immune system derived from white blood cells have been shown to amplify immune system response in human and animal subjects. As suggested, for example, by issued U.S. Pat. Nos. 4,616,079 and 4,468,379, and in copending U.S. patent application Ser. No. 183,905, now abandoned, such amplifiers appear to act on T-helper cells (T4 or T4+ or CD4 cells) in a way that causes them to produce chemical messengers whose effect is to increase the magnitude of or speed up the cell-mediated immune system response to antigens, mitogens, and other means for activating a cell-mediated immune system response. Indicia of this response include production of IL-2 and gamma-interferon, and potentiation or production of cytotoxic cells. The cited references concern the effects of amplifiers of the immune system on T cells and do not discuss B lymphocytes (B cells).

The term "amplifier of the immune system," as used in the preceding paragraph and elsewhere in this patent application (sometime termed "amplifiers" for short), is used in the same sense as that term is used in U.S. Pat. No. 4,710,380; that is a sense that corresponds to that generally understood for the term in the immunological art. The term refers to a product, which may or may not be a single molecular species, that increases (i.e., amplifies) one or more of the following aspects of an immune response in a human or other mammalian body—speed of onset, magnitude, or duration—where the response is nonspecific, the response is to one or more antigens to which the subject has hitherto or is concurrently exposed, the response is attributable to a function of the immune system rather than some other cause, and the response occurs after the introduction of such antigen.

U.S. Pat. No. 4,468,379 specifically refers to the use of amplifiers to augment or accelerate the formation of delayed hypersensitivity reactions to recall antigens. It is understood in the immunological art that such reactions are a reflection of the cell-mediated immunity in which the T4 (CD4) cells play a major role. Those skilled in the immunological art regard delayed hypersensitivity reactions as mediated by T cells, and not by B cells. B cells, and not T4 cells, are considered to mediate antibody (immunoglobulin) production. It is believed that there is no suggestion in the prior art that amplifiers produce results on B cells. (To be sure, it is known that certain T cells are required for the normal production of antibody, but it is generally accepted in the art that the subclass of T cells that affect antibody production are distinct from the subclass of T cells that mediate such cell-mediated immune system phenomena as delayed hypersensitivity reaction to recall antigens. It is believed also that there has been no suggestion in the prior art that a product affecting the activity of the one subclass would have any effect on the activity of the other subclass. In particular, there is no suggestion that amplification of T cell activity will have any effect on B cell activity, such as production of immunoglobulins.)

Thus, those skilled in this art consider that the production of antibodies (immunoglobulins) by B lymphocytes (B cells) in response to antigenic challenge is a separate aspect of immune system response from that aspect considered to involve T4 cells. This B-cell activity is the basis of immunization. At this time, it is common (and legally required in many or most states) routinely to immunize children against such diseases as diphtheria, pertussis, and typhoid (DPT), as well as measles, tetanus, mumps, and other diseases by administering vaccines to them. The B-cell reaction to vaccine is the production of appropriate immunoglobulins, which are intended to confer immunity against the disease. Generally speaking, a particular B cell will be differentiated to produce one particular type of antibody, and such production is caused by the presence in the body of one particular type of antigen. Hence, when a person (or other mammal) has been exposed to a number of different antigens, he, she, or it will have a number of different B cells that can produce their particular immunoglobulins when the appropriate antigen is present.

In some situations, the immune response to antigen is insufficient to confer immunity. That is, a quantity of immunoglobulins is generated (or a number of B cells are potentiated) that is insufficient to confer effective immunity. At other times, an excessive immune reaction may occur, which may be manifested at the time of immunization or later. Excess production of immunogloublins may also occur without human cause. Overproduction of immunoglobulins may cause tissue destruction and autoimmune diseases. It would be desirable to reduce excessive production of immunoglobulins so as to prevent these adverse effects. It is believed that the literature does not describe any practical means of achieving the foregoing result.

It is highly desirable from a medical standpoint to reduce overproduction of immunoglobulins in diseases where such overproduction is present. In particular, it is desirable to reduce the excessive production of immunoglobulins often associated with Acquired Immune Deficiency Syndrome (AIDS) and AIDS-Related Complex (ARC). It is well known that such excessive immunoglobulin production can lead to kidney failure, gangrene, and other highly adverse sequelae. Therefore, lowering abnormally high levels of immunoglobulins in the blood of such patients is therapeutically useful, just as lowering cholesterol levels in the blood of patients at risk for heart attach or stroke is considered therapeutically useful. Physicians, including the first-named inventor, who treat AIDS or ARC patients with very high immunoglobulin levels consider reduction of such levels to be therapeutically useful.

SUMMARY

In principle, the production of immunoglobulins may be increased or decreased by increasing or decreasing (1) the number of immunoglobulin-producing cells, or (2) the amount of immunoglobulin produced by the individual immunoglobulin-producing cells. The present invention accomplishes one or both of these functions by means of administration of amplifier. The inventors have found that even though amplifiers act on T-helper cells there is a further effect, possibly mediated by T-helper cells, on B cells.

The principal effect at which the inventors directed their efforts was the reduction of excessive immunoglobulin production, in AIDS and ARC patients. The inventors found, however, that administration of amplifier could not only reduce excessive immunoglobulin production in those patients otherwise having excessive immune response but administration of amplifier could also increase immunoglobulin production in patients having an insufficient immunoglobulin response. However, the appropriate dosage amounts for decreasing and increasing immunoglobulin production are different, as described in more detail below.

DETAILED DESCRIPTION OF PREFERRED EMBODIMENTS

I. Assay of Immunoglobulin Response

In order to ascertain whether modulation of B-cell response is appropriate in a particular subject, and to titrate administration of amplifier appropriately for that subject, it is desirable to have a method for assaying the subject's immunoglobulin response. The method described below cultures mitogen-exposed cells in the presence and absence of added amplifier. Then the formation of plaque forming cells (PFCs) is assayed by a reverse hemolytic assay to determine whether and to what extent amplifier modulates formation of PFCs. A dose-dependent amplifier modulation of PFC formation is observed. The PFC assay described hereinafter is a modification of a conventional technique; it is believed that PFC assays have not hitherto been utilized to assess effects of the immunomodulators described herein.

Before beginning the assay, various dilutions are prepared of the amplifiers to be used, Imreg Inc. products IMREG-1 TM and ZB-4. TM IMREG-1 is the same product as that which U.S. Pat. No. 4,751,216 refers to as Beta-1.0 (see cols. 2–4), and U.S. Pat. No. 4,616,079 refers to as Amplifier Beta (see Ex. 5, col. 9).

ZB-4 is an endogenous small peptide, and is one of two such small peptides of interest herein. The two such endogenous peptides are the tripeptide Tyr-Gly-Gly and the dipeptide Tyr-Gly. These products, also known as Beta-1.12 and Beta-1.11, are immunologically active components of Beta-1.0, as described in U.S. Pat. No. 4,751,216 (see col. 2, referring to TGG-compound and TG-material). Beta-1.11 and 1.12 have been prepared by the following steps:

(1) extracting Beta Material from leukocytes in accordance with Example 4 of Gottlieb U.S. Pat. No. 4,616,079;

(2) drying such material, reconstituting it in 0.1% trifluoroacetic acid, and injecting it into an octadecylsilane HPLC column;

(3) carrying out HPLC with an ethanol-in-water linear input gradient, starting at 0% ethanol and reaching 50% at 30 minutes;

(4) and monitoring UV absorbance at 254 mm.

Three major UV peaks are observed, which respectively elute at 10.4–10.6 min, 14.0–16.0 min, and 18.0–19.0 min, under the foregoing conditions. The material associated with the middle peak is that which is retained, because biological activity resides almost entirely in such material, which is designated as Beta-1.1. Based on refractive index measurements, the ethanol concentration of the effluent of the second peak was found to be from approximately 0.1% to approximately 0.4%.

The retained Beta-1.1 material was subjected to the following additional steps of HPLC, to extract Beta-1.11 and 1.12: The foregoing Beta-1.1 material was injected into an octadecylsilane resin column. Best results were obtained with a Dupont brand of octadecylsilane resin column (known as ZORBAX TM), which comes packed with a Dupont material containing octadecylsilane groups chemically bonded to silica particles. The solvent system was 100% acetonitrile and 0.05% trifluoroacetic acid aqueous solution, pH 2.5. The following solvent input linear gradients were used: (1) for 15 minutes, from 0%–6% acetonitrile; (2) for 30 minutes, from 6%–40% acetonitrile.

One fraction of interest, hereinafter designated as Beta-1.11, eluted at approximately 23.8 to 24.8 min, for a new column. It was associated with a sharp, narrow peak of UV absorption at 210 nm; this peak is approximately the fourth absorption peak observed (some variability existing), and hence also has been termed "ZB-4." It contains endogenous Tyr-Gly material.

Another fraction of interest, eluted from the material on this HPLC column, but somewhat irregularly, at retention time approximately 22.8–23.2 min. It was associated with a distinct peak of UV absorption at 210 nm, which was a third peak just before the peak associated with Beta-1.11, and which often partially overlapped therewith. This material, referred to as Beta-1.12, contains endogenous Tyr-Gly-Gly material.

IMREG-1 (Beta-1.0) is diluted into a variety of concentrations. Because IMREG-1 is believed to be a mixture of polypeptide materials, phenylalanine, and other products, it is infeasible to express its concentration in Molar terms. However, a standard dosage amount of IMREG-1 for treatment of AIDS and ARC patients to increase their immune response is considered to be that amount of IMREG-1 which is derived from approximately 400,000 human leukocytes (said quantity is also termed 400,000 "cell equivalents"), dispensed in 100 ul (hereinafter the letter u is used in lieu of the Greek letter mu to abbreviate micro) of sterile saline.

It is the practice of Imreg Inc. and the inventor to store IMREG-1 in a preparation (hereinafter referred to at times as a "neat" preparation of IMREG-1) containing $4 \times 10^8$ cell equivalents/ml. Thus, the foregoing standard dosage amount of IMREG-1 is 0.1 ml of a $10^{-2}$ dilution of the neat preparation.

Dilutions of IMREG-1 in RPMI-1640 medium are prepared such that addition of 20 ul of the particular dilution, when added to a total of 1.0 ml of culture, will provide the following final concentrations in the culture:

| Dilution | Cell equivalents/ml culture |
| --- | --- |
| 1:100,000 | 4,000 |
| 1:10,000 | 40,000 |
| 1:5,000 | 80,000 |
| 1:1,000 | 400,000 |
| 1:500 | 800,000 |

ZB-4 is a polypeptide material whose M.W. is approximately 239. It is therefore possible to express its concentration in Molar quantities. ZB-4 is diluted to a variety of concentrations in 20 ul aliquots that include $50\times$ the following: 0.8 pM (picomolar), 8 pM, 16 pM, 80 pM, 160 pM, 800 pM, and 1.6 nM.

There are also 20 ul aliquots of sterile saline with zero concentration of amplifier, for control purposes.

EXAMPLE 1

Cell Culture

Peripheral blood cell populations (hereinafter PBLs) from test subjects are prepared to isolate mononuclear cells, using conventional methods. The PBLs are adjusted to $10^6$ cells/ml in RPM-1640 medium with 25 mM HEPES and L-glutamine (Whittaker Bioproducts), which has been supplemented with 10% heat-inactivated defined fetal bovine serum (Hy-Clone Labs.), 2% PSN Antibiotic (GIBCO Labs., Grand Island, N.Y.) (100×), and 1% extra L-glutamine (GIBCO Labs.) (100×). The resulting PBL mixture is set aside in an ice bucket (4° C.).

5 ml of lyophilized pokeweed mitogen (hereinafter PWM) (GIBCO Labs., Prod. No. 670-5360) is reconstituted with 5 ml sterile cold water. The resulting PWM mixture is set aside.

PWM mixture is added to PBL mixture to provide 10 ul of PWM mixture per ml of PBL mixture. A control with zero PWM is also provided. A number of 1 ml aliquots are dispensed.

Triplicate or quadruplicate cultures are prepared by adding 20 ul aliquots of each of the amplifier concentrations listed above to the 1 ml aliquots of mixture. The resulting mixtures are placed into 12×75 mm polypropylene snap-cap tubes (Falcon, No. 2063). The tubes are cultured with loose caps at 37° C., 5% $CO^2$, for 6 days.

Replicate cultures are pooled. The cells are washed 3× with HBSS (Hanks Balanced Salt Sol., GIBCO, Prod. No. 310-4020). The culture groups are resuspended in 3 ml HBSS and kept on ice until assayed.

EXAMPLE 2

Preparation of Developing Antisera

A fresh anti-human immunoglobulin solution was prepared on the day of the assay from rabbit anti-human immunoglobulin (hereinafter RAI) directed against heavy and light chains of human IgG, IgA, and IgM (U.S. Biochemicals, No. 1169A).

The RAI is received in lyophilized form, is reconstituted with 2 ml sterile distilled water, and is stored at −20° C. until used. It is then diluted in HBSS, 1:400.

EXAMPLE 3

Preparation of Protein A-SRBC Reagent $CrCl_3.6H_2O$ is disolved in 0.9% sterile saline to 250 uM concentration. Protein A (Pharmacia Fine Chem.) is dissolved in 0.9% saline to 0.5 mg/ml concentration. These solutions are set aside. Sheep red blood cells (hereinafter SRBC) (Scott Labs., Fiskeville, R.I.) are washed 3× in 0.9% sterile saline and are left loosely packed in a pellet.

The following are mixed in a 15 ml conical centrifuge tube: 1 ml Protein A solution, 10 ml $CrCl_3$ solution, 1 ml packed SRBC. The tube is incubated at 30° C. for 1 hr on a gently moving shaker. It is then centrifuged at 800×G for 5 min. The supernatant is discarded.

The pellet is washed 1× with 0.9% sterile saline and then 2× with HBSS. The material is then adjusted to 30% (v/v) Protein A-SRBC in HBSS. This preparation of Protein A conjugated with SRBC can be stored at 4° C. for up to 3 days.

The foregoing materials are used in the reverse hemolytic plaque forming cell (hereinafter RHPFC) assay descibed below, which provides a measure of the number of immunoglobulin-producing cells in a sample. The procedure involves culturing activated B cells, which secrete immunoglobulin, in a medium including the Protein A-SRBC reagent of Example 3. When RAI, which contains rabbit immunoglobulin G (IgG) directed toward human immunoglobulins, is added to the culture the RAI reacts with the secreted human immunoglobulin (Ig). The Protein A on the SRBC binds to the RAI-human Ig complex via the IgG of the RAI. When Guinea Pig Complement is then added to the culture and the mixture is further incubated, the SRBC are lysed and a clear area (a "plaque") forms around the B cells that secreted Ig. The number of plaques present is thus a measure of the number of activated B cells.

The RAI reacts with Protein A on the surface of the SRBC. The RAI also reacts with the immunoglobulin produced by the mitogen-stimulated B cells. If RAI concentration is not optimal, complete lysis of the whole plate may occur or no lysis at all may occur. Therefore, it is important to determine, by trial and error, the correct concentration of RAI. In the assay described here, the RAI concentration is, it is believed, optimal for the purpose of the assay.

EXAMPLE 4

RHPFC Assay

A number of Petri plates (60×15 mm) are coated with 4 ml of 2.5% agarose ("Sea Plaque," Marine Colloids, Inc.) and set aside. They may be stored at 4° C. for up to approximately 2 weeks, but must be warmed to room temperature before use in the assay.

A number of glass culture tubes (10×75 mm) are prewarmed to 43° C.

Pooled cultured cell groups of Example 1 are diluted 1:5 in HBSS, and 100 ul is added to each tube. Each tube also receives 250 ul of 1.12% agarose and 25 ul of the Protein A-SRBC reagent of Example 3. Each tube is thoroughly mixed, poured onto one of the coated Petri plates, and gently swirled to distribute the cell mixture into a mono-layer. Triplicate or quadruplicate Petri plate cultures are provided for each amplifier-PWM combination.

When the agarose has solidified, 1 ml of 1:400 RAI of Example 2 is added to the top of each Petri plate so that it completely covers the agarose. The plates are incubated at 37° C. for 1 hr in a humidified 5% $CO_2$ incubator.

1 ml of Guinea Pig Complement (HEMO-LO ™, Cedarlane Labs.), which has been freshly reconstituted in cold sterile water and diluted 1:28 in HBSS, is added to each plate. The plates are then incubated for another 2 hr under the same conditions. The fluid is then aspirated off the top of the plates, which may be stored at 4° C. overnight.

Plaques are denoted as a clear area in the SRBC monolayer bed, which may be observed visually or under a low-power microscope. This represents a zone of lysis around an immunoglobulin-secreting cell. Thus, each plaque represents one B cell that produces immunoglobulin. The number of PFCs per culture is determined by multiplying the number of plaques by the dilution factors. During this assay, the number of cells in each culture group must be counted with a hemacytometer to determine the ratio of PFCs to cultured cells. For greater convenience, the factor PFC per 1000 cells is used, and is hereinafter designated as PFC factor. The PFC factor is proportional to the number of immunoglobulin-producing cells in a specimen.

The foregoing procedure was carried out to provide data for various concentrations of IMREG-1 (with reference to a neat preparation of IMREG-1, i.e., Beta-1.0) used with PBLs from a normal human test subject in the procedure of Example 1.

EXAMPLE 5

Results of RHPFC Assay with IMREG-1

The procedure of Example 4 was carried out with PBLs from a normal human test subject, prepared in accordance with Example 1. Dilutions of IMREG-1 from 1:500 to $10^{-5}$ were used, along with a control (no IMREG-1). Plaques were counted and the following PFC factors were observed for the various dilutions of IMREG-1:

| Dilution of IMREG | PFC Factor |
| --- | --- |
| 0 conc. (control) | 43.7 |
| $10^{-5}$ | 36.2 |
| $10^{-4}$ | 7.68 |
| $2 \times 10^{-4}$ | 31.2 |
| $10^{-3}$ | 50.0 |
| 1:500 | 14.0 |

Thus, as the concentration of IMREG-1 increased toward 1:10,000, the number of immunoglobulin-producing cells decreased toward a minimum of less than 20% of the control result. Then, with further concentrations of IMREG-1, the number of immunoglobulin-producing cells increased to a maximum (at 1:1000) that was approximately 15% over control. Further concentration resulted in another decrease in immunoglobulin-producing cells to a level (32% of control) somewhat above that of the prior minimum. Thus the curve is generally of the form of a cubic equation, $y = a - bx + cx^2 - dx^3$. This "biphasic" result was observed consistently in repetitions of this procedure.

EXAMPLE 6

Results of RHPFC Assay with ZB-4

The procedure of Example 5 was repeated with various concentrations of ZB-4, in place of IMREG-1.

Averaged data for various ZB-4 concentrations showed a generally similar curve. The number of immunoglobulin-producing cells reached a minimum between 1 and 10 pM concentration of ZB-4, and a maximum at from 100 to 150 pM. The maximum PFC factor was from about half again to double the control PFC factor. The minimum PFC factor was from about a quarter to a half the control PFC factor.

In general, the foregoing data indicates that it is possible to use amplifier to reduce by a substantial factor the in vitro immunoglobulin production by a normal human test subject in response to antigenic challenge.

II. Variation on Protocol

The foregoing protocol 1 was then altered to test the in vitro effect of adding amplifiers Beta-1.0 or Beta-1.11 to the culture after B cells had already been potentiated (differentiated). Therefore, no amplifier was mixed with the PWM-activated cells at the outset, as in Example 1. Instead, at the stage where 1.12% agarose and Protein A-SRBC reagent are added (here, the 7th day), 25 ul of different amplifier dilutions is also added to the various replicates. The protocol was otherwise the same.

EXAMPLE 7

Modified RHPFC Assay with ZB-4

The procedure of Example 6 was repeated with the modified protocol just described.

A minimum of immunoglobulin-producing cells was seen at from approximately 0.1 pM to 10 pM concentration of ZB-4. The minimum PFC factor was approximately 35% of the control PFC factor. The maximum was slightly less than the control, and occurred at approximately 300–400 pM concentration.

In general, this further in vitro data suggests that once B-cell potentiation has occurred, the administration of amplifier can modulate the further response but not quite as much as when amplifier is administered concurrently with potentiating the antigen.

III. Effect of Beta-1 on PBLs of Sarcoidosis Patient

IMREG-1 (Beta-1.0 of the cited '216 patent) was administered in vitro to PBLs from a patient suffering from chronic sarcoidosis, in order to determine whether IMREG-1 might be useful to decrease the patient's excess production of immunoglobulins. Sarcoidosis is a disease of unknown origin characterized by granulatomous collections of cells in the lungs, and an associated defect in cell-mediated immune response. Excess immunoglobulin production is seen in patients with this disease.

The protocol for this was similar to that of Examples 1–4, but cells were not cultivated with mitogen. The purpose was to explore the effect of amplifier on the patient's already-activated circulating B cells that were secreting the excess immunoglobulin. A 7-day cell incubation period was used. After incubation, the cells were resuspended in 1.5 ml rather than 3 ml HBSS (see end of Example 1); and the 1:5 dilution of cells (see ¶ 3, Example 4) was omitted, so that 100 ul of undiluted cells are cultured.

EXAMPLE 8

RHPFC Assay of Sarcoidosis Patient

The foregoing protocol was carried out and the following results were observed:

The RHPFC assay showed that at zero concentration of Beta-1.0, i.e., the control, the PFC factor was 0.475. This value is much less than the values obtained with PWM stimulation. (That was to be expected, however, as it represents the patient's B cells that the disease state previously activated.)

At the lowest concentration of Beta-1.0 used, $10^{-8}$ and $10^{-7}$ of the neat preparation, Beta-1.0 caused an increase in the PFC factor to 151% and 90% over control, respectively. Further concentration of Beta-1.0, from $10^{-6}$ to $10^{-4}$, caused a significnt decrease in the PFC factor, with a maximum suppression of 62.7% of control at a concentration of $10^{-5}$ of neat.

A further study was the made to determine the in vitro effect of IMREG-1 (Beta-1.0) on the ability of PFCs of this patient to secrete (produce) antibody. The protocol was varied from that of Examples 1–4, among other ways, in that cells were not cultured with PWM or anything else before the assay.

EXAMPLE 9

Effect of Beta-1.0 on Immunoglobulin Secretion

PBLs of a patient suffering from chronic sarcoidosis were prepared as in Example 1, but were adjusted to $10^6$ cells/ml in HBSS (compare ¶ 1, Example 1). No amplifier or mitogen was mixed with the PBLs and the cells were not cultured at all.

The procedures of Example 4 and Section II were followed, but the 1:5 dilution of cells (see ¶ 3, Example 4) was omitted, so that 100 ul of undiluted cells were mixed with 1.12% agarose and Protein A-SRBC as in ¶ 3, Example 4.

Various dilutions of IMREG-1 in HBSS were provided, including a 0 concentration (control) moiety. Each tube of the preceding paragraph received 25 ul of a concentration (or control), to provide triplicate cultures. The plates were incubated as described in Example 4, using RAI and HEMO-LO ™ Guinea Pig Complement as described there. The cultures were then assayed, as described above, and PFC factor versus dilution was tabulated.

At a dilution of $5 \times 10^{-8}$ neat, a minimum PFC factor that was 31% of control was observed, indicating a substantial reduction of immunoglobulin production.

This data is generally comparable with that of Section II, above, involving use of ZB-4 (Beta-1.11) to modulate mitogen-potentiated normal PBLs; here, of course, the B-cell potentiation is supplied by the patient's disease rather than by our addition of mitogen. The data suggested that administration of an appropriate dosage of IMREG-1 in vivo should decrease the patient's excess immunoglobulin production in the direction of normal.

IV. Effect of Beta-1 on AIDS/ARC patients—In vivo data

One of the characteristic symptoms of Acquired Immune Deficiency Syndrome (AIDS) and AIDS-Related Complex (ARC) is a high serum immunoglobulin level. The etiology is not well understood, but it is believed that the excess immunoglobulin production represents an autoimmune reaction. It is believed that the presence of these high immunoglobulin levels can cause kidney failure and gangrene, among other adverse sequelae. Therefore, it is believed therapeutically advantageous to reduce the levels towards the normal range.

The following actual patient data has been submitted to FDA.

EXAMPLE 10

AIDS/ARC Patient Data, Effect of IMREG-1 on Ig Levels

A group of 14 patients with AIDS or ARC were treated biweekly with a standard dosage of IMREG-1 (Beta-1.0), until six doses were given. All 14 initially had elevated IgG production and 13 also had elevated IgA production.

Data was averaged for the 14 high-IgG and 13 high-IgA patients.

Initial IgG and IgA readings were, respectively, approximately 3200 mg/dl and 420 mg/dl. The "best straight-line" (least squares) trend was downward to approximately 2800 mg/dl and 380 mg/dl, respectively, at one week after the sixth dose.

(If a non-straight line model is attempted, the general trend remains downward, to a still lower level than stated above, but there are early-week increases over the initial levels.)

It is thus seen that administration of IMREG-1 to a set of AIDS or ARC patients having elevated IgG and IgA blood levels reduced their IgG and IgA production. This treatment was considered therapeutically useful to these patients, since the treatment reduced their risk of kidney failure, gangrene, and other adverse sequelae associated with excessive Ig production.

Since it is known that ZB-4 is a therapeutically active, more potent moiety of IMREG-1, it is to be expected that similar reduction of Ig levels can be obtained by administration of ZB-4. The relation between a standard dosage of IMREG-1 and ZB-4 is known. For example, 1 fg of Beta-1.11 (essentially Tyr-Gly) or Beta-1.12 (essentially Tyr-Gly-Gly) has approximately the same immunological activity as 5–10 fg of Beta-1.0. Also, the therapeutic equivalent of one standard dosage of Beta-1.0 (IMREG-1) for an 80 kg adult male person is approximately 1 to 400 pg of Beta-1.11 (essentially Tyr-Gly) or Beta-1.12 (essentially Tyr-Gly-Gly). This data leads to the following further examples.

EXAMPLE 11

AIDS/ARC Patients, Effect of ZB-4 on Ig Levels

A group of patients with AIDS or ARC are treated biweekly with 50 pg of ZB-4, according to the protocol of Example 10.

Substantially the same results are observed as were observed in Example 10.

EXAMPLE 12

AIDS/ARC Patients, Effect of Beta-1.11 on Ig Levels

A group of patients with AIDS or ARC are treated biweekly with 50 pg of Beta-1.11, according to the protocol of Example 10.

Substantially the same results are observed as were observed in Example 10.

EXAMPLE 13

AIDS/ARC Patients, Effect of Beta-1.12 on Ig Levels

A group of patients with AIDS or ARC are treated biweekly with 50 pg of Beta-1.12, according to the protocol of Example 10.

Substantially the same results are observed as were observed in Example 10.

V. Relation of Assay and In vivo Administration

The variability of the data and the complexity of the response curve suggest that it would be preferable to titrate patient dosage on an individual basis, if possible. In principle, if patient A's PBLs show a minimum PFC at $10^{-5}$ dilution of a given amplifier, while those of patient B show a minimum PFC at $10^{-4}$ dilution of that amplifier, the appropriate in vivo dosage amount of that amplifier to reduce patient A's immunoglobulin production should be less than the appropriate dosage amount for patient B. Ideally, such an assay would permit calculation of the appropriate dosage amount for a patient in terms of pg of amplifier/kg of body weight.

In practice, however, this is highly problematical. The in vitro systems appear only moderately to mimic the in vivo system. The in vitro systems of the assay are relatively "inefficient," compared to the in vivo human immune system. Thus, the inventors have observed that it requires approximately the equivalent of 114,000 cells/ml (i.e., the amount of Beta-1.0 derived from that many leukocytes) to produce an in vitro effect in the foregoing procedures. On the other hand, a therapeutic dose for an AIDS/ARC patient is 400,000 cell equivalents. Assuming an 80 kg body (approximately 80,000 ml, mostly water), the in vivo concentration for therapy is approximately 5 cell equivalents/ml. Thus, the ratio between in vivo and in vitro observed effectiveness of IMREG-1 is approximately 22,800:1.

For this reason, it has not been possible at this time to derive a formula relating the amplifier concentration producing a minimal PFC factor and the appropriate therapeutic dose for modulating immunoglobulin production. However, the assay is believed probative of whether a test subject's B cells can be modulated by dosage with amplifier, as contrasted, for example, with their having a defect that cannot respond to amplifier treatment.

As for determining the proper dosage amount to use, clinical experiments such as those described above have resulted in more general estimates of what constitutes an effective dosage amount of amplifier for immunoglobulin modulation. At this time, it is believed that 20-80 pg of Beta-1.11 (essentially Tyr-Gly) or Beta-1.12 (essentially Tyr-Gly-Gly) represents a therapeutic dosage for an 80 kg person. The following Examples more specifically described effective dosage amounts for immunodefective conditions involving inappropriate immunoglobulin production. The pg/kg figures should be understood to be approximate, and subject to modification on the basis of individual physician discretion, and they should be titrated over time on the basis of the physician's observation of the patient's clinical progress. It should be noted also, that 1 standard dosage amount of IMREG-1 (Beta-1.0) for patients is equivalent to approximately a 20-80 pg dose of ZB-4 (Beta-1.11).

EXAMPLE 14

Titration of Amplifier Dosage

A patient suffers from AIDS or ARC, and he has an elevated serum immunoglobulin (IgG) level (greater than 1400 mg/dl), indicative to the attending physician of excessive immunoglobulin production. The physician considers it therapeutically desirable to lower the patient's level of immunoglobulin production.

The physician assays the patient's immunoglobulin response by the protocol of Examples 1-4, or alternative as in Example using ZB-4 (Beta-1.11). The patient weighs 80 kg. The physician therefore administers intradermal injections of 20 to 80 pg of ZB-4 (0.25 to 1 pg/kg of body weight) in sterile saline, biweekly, for eight weeks, and then retests. (The appropriate amount is determined by trial and error, and is subject to the physician's discretion. It is believed that 0.25 pg/kg is an appropriate starting point for such trial and error determination in the case of excessive Ig production.)

The patient's serum immunoglobulin (IgG) level is now lower (1280 mg/dl), which is considered within the high normal range. The physician continues the same treatment, retesting every three months.

EXAMPLE 15

Another Titration of Amplifier Dosage

A patient suffers from common variable immunodeficiency, and he has an lowered serum immunoglobulin (IgG) level (350 ml/dl), indicative to the attending physician of insufficient immunoglobulin production. The physician considers it therapeutically desirable to raise the patient's level of immunoglobulin production.

The patient weighs 80 kg. The physician therefore administers intradermal injections of 20 to 80 pg of ZB-4 (0.25 to 1 pg/kg of body weight) in sterile saline, biweekly, for eight weeks, and then retests. (The appropriate amount is determined by trial and error, and is subject to the physician's discretion. It is believed that 1 pg/kg is an appropriate starting point for such trial and error determination in the case of insufficient Ig production.)

The patient's serum immunoglobulin level (IgG) is now higher (710 mg/dl), which is considered within the low normal range. The physician continues the same treatment, retesting every three months.

The foregoing diseases are examples of those which may advantageously be treated by administration of amplifier to modulate immunoglobulin production. The scope of the invention includes other such diseases, as well. Illustrative examples of diseases or pathological conditions to which the procedure of Example 14 applies are: lupus, sarcoidosis, AIDS, ARC, and hyperglobulinemic states. Illustrative examples of diseases or patholgical conditions to which the procedure of Example 15 applies are: common variable immunodeficiency, severe combined immunodeficiency, and X-linked agammaglobulinemia.

VI. Immunization with Vaccines

As indicated earlier, a potential problem involved in immunization by vaccination is insufficient production of immunoglobulin to confer an immunity. It is therefore advantageous to use appropriate amounts of amplifier to prevent or counteract these tendencies. This may advantageously be accomplished either by concurrently injecting amplifier with the vaccine, or by including amplifier in the same vial or at least in the same syringe to avoid multiple injections.

For example, malaria vaccines are often ineffective because the subject who is vaccinated does not produce sufficient immunoglobulin in response to the vaccine to develop immunity. Other examples of vaccination procedures where it could be medically advisable to administer an amplifier to increase immunoglobulin production are American trypanosomiasis and leishmaniasis, among others, as well as certain veterinary diseases such as pseudorabies in pigs. In regard to these diseases, of which malaria is exemplary, it is necessary to cause an increased antibody production in order to secure a successful vaccination against the disease.

EXAMPLE 17

Malaria

A physician desires to immunize an 80 kg person against malaria. The physician therefore concurrently administers with the vaccine an intradermal injection of 20 pg of ZB-4 (Beta-1.11) in sterile saline. (It may be necessary to increase the amount of ZB-4, by case-by-case trial and error methods, to approximately 80 pg.)

A physician may also be concerned that administration of a dosage amount of an antigen may provoke excessive immunoglobulin production in a particular patient. The physician may therefore decide to administer an appropriate dosage amount of amplifier (for example, 0.25 pg ZB-4/kg body weight) concurrently with the antigen.

GENERAL CONCLUDING REMARKS

It is thus seen that administration of amplifier can modulate B-cell activity, as well as T-helper cell activity.

The in vitro and in vivo data described above indicates that administration of amplifier to patients, such as AIDS or ARC patients, suffering (or believed likely to begin to suffer) from elevated levels of immunoglobulin production will beneficially reduce their immunoglobulin production to less harmful levels. The data provided above is based on use of IMREG-1 and its derivative ZB-4, which correspond to Beta-1.0 of the cited '216 patent and Beta-1.11 described at the beginning of section I of this specification. It is reasonable to conclude that similar results may be obtained by means of using other derivatives of Beta-1.0, such as Beta-1.12 described at the beginning of section I of this specification, and similar products such as amplifiers Zeta-2 and Eta, or other amplifiers.

There are a relatively few number of amplifiers known in the immunological art. It is known what is the relation of the effective dosage amount of one of them to that of another of them, and the Beta-1.0/Beta-1.11/Beta-1.12 equivalencies are expressly stated above. The procedures described above can thus be carried out with an available or desired amplifier by using the latter in an amount dictated by the ratio of its effective dosage amount to the effective dosage amount of amplifier described hereinabove, which does not require any substantial experimentation. This procedure is illustrated in Examples 10 to 14.

Similarly, primary attention has been focussed hereinabove on two purified forms of the Beta family of amplifiers (comprising Beta-1.0, Beta-1.11 [which is essentially Tyr-Gly], and Beta-1.12 [which is essentially Tyr-Gly-Gly]), namely Tyr-Gly and Tyr-Gly-Gly. But it will be appreciated by those skilled in the art that it should be expected that the common pharaceutical salts, esters, and derivatives of that dipeptide and that tripeptide will have similar properties and be similarly useful. It is well known in pharmaceutical arts that salts and esters of active pharmaceuticals ordinarily possess comparable, and sometimes enhanced, pharmaceutical activity relative to the unmodified molecule. The same applies to the common molecular manipulations of pharmaceutical molecules, such as amidification, methylation, and preparation of similar derivatives. Also, it is well established that an active pharmaceutical can be and typically is formulated with different salts, such as the sodium and potassium forms of penicillin, or the use of citrate, acetate, or HCl forms. Persons skilled in the art expect such expedients, which are too numerous either to list individually or claim one-by-one without unduly multiplying the claims.

The data set forth above in the specification also suggests that administration of amplifier may be beneficial to increase immunoglobulin production in patients suffering from insufficient immunoglobulin production. In this case, the dosage range is substantially higher than that to be used for decreasing immunoglobulin production, but it must, of course, be lower than those still higher levels of dosage that once again decrease immunoglobulin production. This is due to the "biphasic" or cubic-equation relationship of effect vs. concentration, which is described in the specification with numerical detail for particular amplifiers. See also Example 16.

The human data may be extrapolated to horses, cows, and other mammals, correcting for the body weight of the animal in accordance with recognized veterinary procedures.

The foregoing examples are intended to be illustrative only and not exhaustive of the scope of the invention.

As used in the claims, antigen includes mitogen.

Where other terms are used in the claims that have been defined above in the specification, the meaning of the terms in the claims is that given them in the specification.

The subject matter claimed is:

1. A method of decreasing quantity of immunoglobulin produced by B-cells of a human or other mammalian subject in response to antigen, where said subject suffers from a disease or condition in which excessive immunoglobulin production occurs, comprising administering to said subject an effective dosage amount of an amplifier of the immune system, said amount being effective to decrease said quantity of immunoglobulin, and said ampifier being Beta-1.0, Beta-1.11, or Beta-1.12.

2. The method of claim 1 wherein said subject suffers from AIDS or ARC.

3. A method of decreasing quantity of immunoglobulin produced by B-cells of a human or other mammalian subject in response to antigen, where said subject suffers from a disease or condition in which excessive immunoglobulin production occurs, comprising administering to said subject an effective dosage amount of an amplifier of the immune system, said amount being effective to decrease said quantity of immunoglobulin, and said ampifier being Tyr-Gly or Tyr-Gly-Gly.

4. The method of claim 3 wherein said subject suffers from AIDS or ARC.

* * * * *